United States Patent [19]

Nakamura et al.

[11] Patent Number: 5,045,109
[45] Date of Patent: Sep. 3, 1991

[54] HIGH CONCENTRATION HERBICIDE FORMULATION

[75] Inventors: Kanji Nakamura, Shimizu; Susumu Katou, Shizuoka, both of Japan

[73] Assignee: Kumiai Chemical Industry Co., Ltd., Tokyo, Japan

[21] Appl. No.: 483,865

[22] Filed: Feb. 23, 1990

[30] Foreign Application Priority Data

Mar. 13, 1989 [JP] Japan .................................. 64-60440

[51] Int. Cl.$^5$ ..................... A01N 37/00; A01N 43/40; A01N 43/36; A01N 43/38
[52] U.S. Cl. ........................................ 71/100; 71/88; 71/94; 71/95; 71/96; 71/DIG. 1; 523/122
[58] Field of Search ................... 71/100, D 1, 88, 94, 71/95, 96; 523/122, 176

[56] References Cited

U.S. PATENT DOCUMENTS 4,382,115  5/1983  Takahashi .................. 428/424.6
4,936,901  6/1990  Sugant, Sr. et al. ................ 71/92

OTHER PUBLICATIONS

Chem. Abstracts, "Photochemistry of Thiocalbamate Herbicides...", Ruzo et al., vol. 102, #108082S (1985).

*Primary Examiner*—Alan Siegel
*Assistant Examiner*—Jessica H. Nguyen
*Attorney, Agent, or Firm*—Oblon, Spivak, McClelland, Maier & Neustadt

[57] ABSTRACT

A high concentration herbicide formulation comprising (1) a herbicidally active thiolcarbamate of the following formula I which is liquid at room temperature, (2) at least one nonionic surfactant of the following formula II and (3) an anionic surfactant of the following formula III:

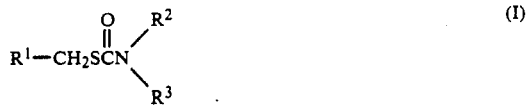

wherein $R^1$ is an alkyl group having from 1 to 3 carbon atoms, a phenyl group or a halogen-substituted phenyl group, $R^2$ is an alkyl group having from 1 to 5 carbon atoms, and $R^3$ is an alkyl group having from 1 to 5 carbon atoms, provided that $R^2$ and $R^3$ may form a ring;

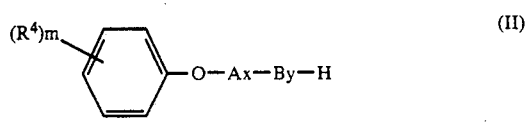

wherein $R^4$ is

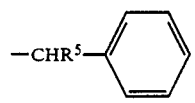

wherein $R^5$ is a hydrogen atom or a methyl group, m is an integer of from 1 to 3, x is an integer of at least 10, y is an integer of from 0 to 10, provided that x+y is within a range of from 10 to 30, A is an oxyethylene group, and B is an oxypropylene group, provided that the addition form of A and B may be a block-form or a random-form; and

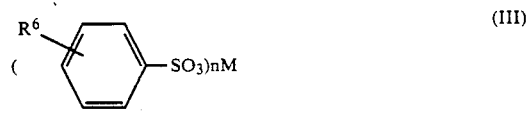

wherein $R^6$ is an alkyl group having from 9 to 15 carbon atoms, M is an alkali metal or an alkaline earth metal, and n is the number of metal ions.

4 Claims, No Drawings

HIGH CONCENTRATION HERBICIDE FORMULATION

The present invention relates to a high concentration herbicide formulation excellent in the emulsifying stability, which comprises a herbicidally active ingredient and a small amount of surfactants.

As thiolcarbamate herbicides, commercial products are available such as those known by common names Thiobencarb, Orbencarb, Esprocarb, Morinate and EPTC, and they are very useful for controlling gramineous weeds which are strongly hazardous weeds. These thiolcarbamate herbicides are used mainly in the form of granules for direct application and in the form of emulsifiable concentrates to be diluted for use.

Conventional emulsifiable concentrates are prepared usually by employing an organic solvent and a surfactant. However, use of an organic solvent brings about various problems including a safety problem to the users of the agricultural chemical because of the phytotoxicity of the organic solvent, a storage problem due to the inflammability of the organic solvent, an environmental pollution problem by its application and a phytotoxicity to crop plants. Further, in order to emulsify and disperse not only the active ingredient but also the organic solvent used, a surfactant is used in a large amount, whereby there will be an economical problem as well as a problem of environmental pollution by the surfactant.

Therefore, for an emulsifiable concentrate, it is desired to essentially solve the above-mentioned various problems attributable to the organic solvent and the surfactant.

A wettable powder and a flowable formulation are conceivable as the types of formulation which may be substituted for the emulsifiable concentrate. However, the wettable powder has a problem of dusting at the time of dilution, and there is a possible danger to the safety of the users. Besides, in the case of a liquid active ingredient, it is difficult to obtain a highly concentrated formulation as compared with the emulsifiable concentrate. A granulated wettable powder has also been proposed to prevent dusting at the time of dilution, but in the case where the active ingredient is liquid, such a method still has a drawback that it is difficult to obtain a formulation having a high concentration. On the other hand, a flowable formulation prepared by having a solid active ingredient suspended and dispersed in water or having a liquid active ingredient emulsified and dispersed in water, usually contains an organic solvent such as ethylene glycol or propylene glycol to impart freeze resistance. Accordingly, it has a problem attributable to such an organic solvent. Further, it has a problem that the freeze resistance is inadequate at an extremely cold area of $-20°$ C. or lower, whereby it freezes, and when returned to room temperature, the dispersion system will be destroyed, and separation or precipitation will result. Further, in many cases, a flowable formulation is adjusted to have a high viscosity to improve the storage stability at room temperature, whereby the handling at the time of use often tends to be difficult.

As a conventional technique to obtain a highly concentrated emulsifiable concentrate without using an organic solvent, there is a case wherein an oily active ingredient and a polyoxyalkylene ether are mixed (Japanese Examined Patent Publication No. 45370/1978) or a case wherein an active ingredient and a sulfate salt of a nonionic surfactant are used as essential components (Japanese Examined Patent Publication No. 39561/1988). However, in these cases, the active ingredients are mainly organic phosphorus insecticides or fungicides, and they have a drawback that a large amount of the surfactant is required relative to the active ingredient. In fact, when a herbicidally active ingredient of thiolcarbamate type which is liquid at room temperature is formulated into an emulsifiable concentrate using the above surfactant only, a large amount of the surfactant is required, and yet the stability of the diluted solution is inadequate.

On the other hand, as a conventional technique for a combination of a common polyoxyalkyleneallyphenyl ether and a metal salt of an alkylbenzene sulfonic acid, a combination of an organic phosphorus agricultural chemical and a plague preventive emulsifier (Japanese Examined Patent Publication No. 16920/1969) or a combination of an agricultural chemical and a plague preventive emulsifier (Japanese Examined Patent Publication No. 181320/1969) is known. However, these combinations are concerned primarily with organic phosphorus agricultural chemicals. Besides, they are concerned with emulsification techniques using organic solvents.

Thus, it is strongly desired to develop an agricultural chemical formulation whereby a herbicidally active thiolcarbamate ingredient useful for controlling agriculturally hazardous gramineous weeds can be diluted and applied without the above-mentioned problems attributable to an organic solvent or a surfactant.

It is ideal that the herbicidally active ingredient of thiolcarbamate type can be diluted directly with water and applied without using an organic solvent and a surfactant. However, the compound of this series is hydrophobic, and it is difficult to dissolve or disperse it in water by itself. Accordingly, it is an object of the present invention to provide a formulation having excellent emulsifiability under various application conditions, such as a wide range of dilution, various qualities of water used for dilution and various temperatures of water, by an addition of a very small amount of a surfactant per unit weight of the active ingredient.

The present inventors have conducted extensive researches to overcome the above mentioned problems attributable to an organic solvent or a surfactant in formulating a herbicidally active ingredient of thiolcarbamate type into an emulsifiable concentrate, and as a result, have found it possible to prepare a formulation having excellent emulsified stability without using an organic solvent, by simply combining certain specific surfactants in certain specific proportions to the herbicidally active ingredient of thiolcarbamate type, even in a small amount. The present invention has been accomplished on the basis of this discovery.

Thus, the present invention provides a high concentration herbicide formulation comprising (1) a herbicidally active thiolcarbamate of the following formula I which is liquid at room temperature, (2) at least one nonionic surfactant of the following formula II and (3) an anionic surfactant of the following formula III:

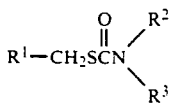

wherein $R^1$ is an alkyl group having from 1 to 3 carbon atoms, a phenyl group or a halogen-substituted phenyl group, $R^2$ is an alkyl group having from 1 to 5 carbon atoms, and $R^3$ is an alkyl group having from 1 to 5 carbon atoms, provided that $R^2$ and $R^3$ may form a ring;

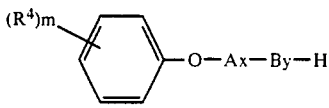

wherein $R^4$ is

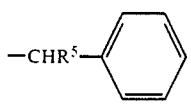

wherein $R^5$ is a hydrogen atom or a methyl group, m is an integer of from 1 to 3, x is an integer of at least 10, y is an integer of from 0 to 10, provided that $x+y$ is within a range of from 10 to 30, A is an oxyethylene group, and B is an oxypropylene group, provided that the addition form of A and B may be a block-form or a random-form; and

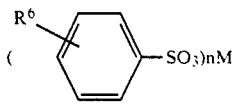

wherein $R^6$ is an alkyl group having from 9 to 15 carbon atoms, M is an alkali metal or an alkaline earth metal, and n is the number of metal ions.

Now, the present invention will be described in detail with reference to the preferred embodiments.

The compound of the formula I includes the following compounds. The compound Nos. will be referred to hereinafter.

Compound (1): S-(4-chlorobenzyl)-N,N-diethylthiolcarbamate (common name: Thiobencarb)

Compound (2): S-(2-chlorobenzyl)-N,N-diethylthiolcarbamate (common name: Orbencarb)

Compound (3): S-benzyl 1,2-dimethylpropyl(methyl)-thiolcarbamate (common name: Esprocarb)

Compound (4): S-ethyl-hexahydro-1H-azepine-1-carbothioate (common name: Morinate)

Compound (5): S-ethyl-N,N-di-n-propylthiolcarbamate (common name: EPTC)

The nonionic surfactants used in the present invention are represented by the above formula II. Preferred are nonionic surfactants having a HLB value within a range of from 12 to 15.

For the calculation of the HLB value, there are many methods. However, for the purpose of the present invention, the HLB value is the one calculated by a method which is usually called an atrass method. According to the atrass method, the HLB value is calculated by the following equation for a nonionic surfactant having, as hydrophilic groups, polyoxyethylene groups only. (Here, the influence by the polyoxypropylene groups is neglected.)

HLB value =
Weight proportion of oxyethylene groups ÷ 5

Further, in the case where two or more nonionic surfactants of the formula II are used in combination, the HLB value of the surfactant mixture is represented by the arithmetic mean based on the blend ratios i.e. by the following equation.

$$HLB_{12} = (HLB_1 \times W_1 + HLB_2 \times W_2) \div (W_1 + W_2)$$

where $HLB_{12}$ is the HLB value of the surfactant mixture, HLB1 and HLB2 are the HLB values of the respective surfactants, and $W_1$ and $W_2$ are the weights of the respective surfactants.

The anionic surfactants used in the present invention are metal salts of alkylbenzene sulfonic acids of the above formula III.

Particularly preferred as the anionic surfactant is a calcium salt of dodecylbenzene sulfonic acid.

When the surfactant of the formula II or III is used alone as an emulsifier for the thiolcarbamate herbicide, the emulsifiability of the resulting emulsifiable concentrate is poor.

Whereas, when the surfactants of the formulas II and III are used in combination as emulsifiers for the thiolcarbamate herbicide, surprisingly excellent emulsifiability is obtained.

The amounts or proportions of the nonionic surfactant (N) and the anionic surfactant (A) blended to the formulation may optionally be changed. However, in order to obtain satisfactory emulsified stability irrespective of the degree of dilution, the quality of water or the change in the temperature of water, the total amount of (N)+(A) is preferably within a range of from 3 to 15 parts by weight per 100 parts by weight of the herbicidally active ingredient. Further, the weight proportions of the surfactants (N) and (A) may vary depending upon the herbicidally active ingredient of thiolcarbamate type, but they are preferably within the ranges of (N) = 50 to 70% by weight and (A) = 50 to 30% by weight. Thus, it is possible to obtain a highly concentrated herbicidal formulation which has never been available before and which is highly safe to the users with the adverse effects to the environment reduced.

If necessary, the high concentration herbicide formulation of the present invention may further contain up to 5 parts by weight of physical adjuvants per 100 parts by weight of the herbicidally active ingredient. The physical adjuvants include, for example, a solidifying point depressant including a phenol such as bisphenol A, resorcin, catechol or hydroquinone and an alcohol such as benzyl alcohol; a viscosity controlling agent including a vegetable oil such as soybean oil, rape seed oil or corn oil, an animal oil such as whale oil, a mineral oil such as liquid paraffin and a plasticizer such as dioctyl phthalate (DOP), dioctyl azipate (DOA) or dioctyl sebacate (DOS); and a stabilizer including an antioxidant such as 2,6-di-tert-butyl-4-methylphenol (BHT) and a decomposition preventing agent such as isopropyl phosphate (PAP). The herbicide formulation of the present invention may further contain other herbicidally active components or other surfactants, as the case requires.

The high concentration herbicide formulation of the present invention can be prepared in accordance with a usual method for the preparation of an emulsifiable concentrate. A uniform emulsifiable concentrate composition can be obtained merely by mixing the above described materials. Therefore, it can readily be prepared as compared with a wettable powder or a flowable formulation.

Now, the present invention will be described in further detail with reference to Examples. However, it should be understood that the present invention is by no means restricted to such specific Examples. In these Examples, "parts" means "parts by weight".

EXAMPLE 1

To 93 parts of Compound (1), 4.8 parts of polyoxyethylene (16 mol) tristyrene-modified phenyl ether (HLB=12.5) and 2.2 parts of magnesium dodecylbenzene sulfonate were added and mixed to obtain a high concentration herbicide formulation of the present invention.

EXAMPLE 2

To 97 parts of Compound (1), 1.2 parts of polyoxyethylene (24 mol) distyrene-modified phenyl ether (HLB=14.4), 0.6 part of polyoxypropylene (2 mol) polyoxyethylene (14 mol) distyrene-modified phenyl ether (HLB)=12.1) and 1.2 parts of calcium dodecylbenzene sulfonate were added and mixed to obtain a high concentration herbicide formulation of the present invention.

EXAMPLE 3

To 95 parts of Compound (2), 3.3 parts of polyoxyethylene (27 mol) styrene-modified phenyl ether (HLB=14.9) and 1.7 parts of calcium dodecylbenzene sulfonate were added and mixed to obtain a high concentration herbicide formulation of the present invention.

EXAMPLE 4

To 95 parts of Compound (3), 2.3 parts of polyoxypropylene (6 mol) polyoxyethylene (22 mol) distyrene modified phenyl ether (HLB=14.1), 0.9 part of polyoxypropylene (2 mol) polyoxyethylene (16 mol) distyrene-modified phenyl ether (HLB=12.7) and 1.8 parts of calcium dodecylbenzene sulfonate were added and mixed to obtain a high concentration herbicide formulation of the present invention.

EXAMPLE 5

To 95 parts of Compound (4), 2.6 parts of polyoxyethylene (20 mol) tristyrene-modified phenyl ether and 2.4 parts of calcium dodecylbenzene sulfonate were added and mixed to obtain a high concentration herbicide formulation of the present invention.

EXAMPLE 6

To 75 parts of Compound (1), 13 parts of 2-methylthio-4,6-bis(ethylamino)-S-triadine (common name: symmetrine) and 7 parts of ethyl 2-methyl-4-chlorophenoxy-butyrate (common name: MCPB E), 1.3 parts of polyoxypropylene (2 mol) polyoxyethylene (22 mol) tristyrene-modified phenyl ether (HLB=12.0), 1.6 parts of polyoxypropylene (5 mol) polyoxyethylene (13 mol) distyrene-modified phenyl ether and 2.1 parts of calcium dodecylbenzene sulfonate were added and mixed to obtain a high concentration herbicide formulation of the present invention.

EXAMPLE 7

To 93 parts of Compound (1), 7 parts of Newkalgen 902-A (a blend product of polyoxyalkylenestyrylphenyl ether and a metal salt of dodecylbenzenesulfonic acid, manufactured by Takemoto Yushi K.K.) was added and mixed to obtain a high concentration herbicide formulation of the present invention.

EXAMPLE 8

To 62 parts of Compound (1), 32 parts of 3,4-dichloropropionaniride, 1.5 parts of polyoxyethylene (19 mol) tristyrene-modified phenyl ether (HIB: 12.5), 2.2 parts of calcium dodecylbenzene sulfonate and 2.3 parts of polyoxyethylene (34 mol) nonylphenyl ether were added and mixed to obtain a high concentration herbicide formulation of the present invention.

COMPARATIVE EXAMPLE 1

To 55 parts of Compound (1), 10 parts of Sorpol SNX (manufactured by Toho Chemical Industries Company Limited) and 35 parts of xylene were added and mixed to obtain a comparative emulsifiable concentrate composition.

COMPARATIVE EXAMPLE 2

To 55 parts of Compound (1), 2.8 parts of a polyalkylene glycol (Sorpol 670, manufactured by Toho Chemical Industries Company Limited), 1.05 parts of polyalkylene glycol (Sorpol 671, manufactured by Toho Chemical Industries Company Limited) and 1.05 parts of polyoxyethylenealkylallyl ether (Sorpol 685, manufactured by Toho Chemical Industries Company Limited) were added and mixed. Then, 37 parts of city water and 3.1 parts of ethylene glycol were added thereto. The mixture was stirred at 10,000 rpm for 10 minutes for emulsification to obtain a comparative aqueous emulsifiable concentrate composition.

COMPARATIVE EXAMPLE 3

To 93 parts of Compound (1), 4.5 parts of oxypropylene (n=2) polyoxyethylene (n=9) addition styrene (n=2)-modified o-phenylphenol (HLB=9.9) and 2.5 parts of calcium dodecylbenzene sulfonate were added and mixed to obtain a comparative emulsifiable concentrate composition. (Exemplifying the surfactant disclosed in Japanese Examined Patent Publication No. 18320/1969)

COMPARATIVE EXAMPLE 4

To 93 parts of Compound (1), 4.55 parts of polyoxyethylene (35 mol) addition (2 mol) styrene-modified o-phenylphenol (HLB=15.8) and 2.45 parts of calcium dodecylbenzene sulfonate were added and mixed to obtain a comparative emulsifiable concentration composition. (Exemplifying the surfactant disclosed in Japanese Examined Patent Publication No. 18320/1969)

COMPARATIVE EXAMPLE 5

To 93 parts of Compound (1), 7 parts of polyoxypropylene (n=10) polyoxyethylene (n=5) styrene-modified phenol ether calcium sulfate was added and mixed to obtain a comparative emulsifiable concentrate composition. (Exemplifying the surfactant disclosed in Japanese Examined Patent Publication No. 39561/1988)

COMPARATIVE EXAMPLE 6

To 93 parts of Compound (1), 7 parts of polyoxyethylene (11.8 mol) benzyl-o-phenylphenol ether was added and mixed to obtain a comparative emulsifiable concentrate composition. (Exemplifying the surfactant disclosed in Japanese Examined Patent Publication No. 45370/1978)

The high concentration herbicide formulation of the present invention has good emulsified stability without being influenced by the degree of dilution, the nature of water or the temperature of water and can be used consistently in various countries of the world. Also from the aspect of cold resistance, it is an excellent formulation in that although it freezes at a temperature lower than the solidifying point of the herbicidally active ingredient used, no separation or precipitation is observed when returned to room temperature, and no degradation of the emulsifiability is observed.

The high concentration herbicide formulation of the present invention employs no organic solvent, and there is no danger of inflaming during its preparation, or there is no problem such as poisoning by a solvent to the users or toxicity to human or animals, as compared with the conventional emulsifiable concentrate or flowable formulation (aqueous emulsifiable concentrate formulation) employing an organic solvent. Further, it is thereby possible to avoid a danger of fire during the transportation of the products or during the storage or maintenance of the products, and the users can use it safely. Further, there is no danger of phytotoxicity to crop plants, and the selectivity is excellent. Also, the influence over the ecosystem by organic solvents or surfactants can thereby be reduced.

The amounts of surfactants added are small, whereby it is possible to obtain a composition wherein the content of the herbicidally active ingredient is very high. This is advantageous from the viewpoint of transportation, and it is also suitable for application in a small amount at a high concentration.

Now, the effects of the high concentration herbicide formulation of the present invention will be described with reference to Test Examples.

TEST EXAMPLE 1: Test for emulsifiability

Using a cylinder having capacity of 100 ml and equipped with a stopper, the initial emulsifiability and the emulsified stability after reversing it 30 times for 1 hour and after being left to stand still for 2 hours and 24 hours, were examined under the following test conditions. The results are shown in Table 1 (temperature of water: 10° C.) and in Table 2 (temperature of water: 30° C.).

Test conditions

Nature of water: Hard water of 3°, hard water of 19.2°
Temperature of water: 10° C., 30° C.
Degree of dilution: 20 times, 200 times Evaluation method Initial emulsifiability
○: Self emulsifiability
Δ: Slightly poor self emulsifiability
X: Poor self emulsifiability Emulsified stability ○: No separation or precipitation
Δ: Separation and precipitation not more than 2 mm
X: Separation and precipitation more than 2 mm

TABLE 1

(Temperature of water: 10° C.)

| | Initial emulsifiability | | | | Emulsified stability | | | | | | | |
|---|---|---|---|---|---|---|---|---|---|---|---|---|
| | Hard water of 3° | | Hard water of 19.2° | | Hard water of 3° | | | | Hard water of 19.2° | | | |
| | | | | | After 2 hours | | After 24 hours | | After 2 hours | | After 24 hours | |
| Example No. | ×20 | ×200 | ×20 | ×200 | ×20 | ×200 | ×20 | ×200 | ×20 | ×200 | ×20 | ×200 |
| Example 1 | ○ | ○ | ○ | ○ | ○ | ○ | ○ | ○ | ○ | ○ | ○ | ○ |
| Example 2 | ○ | ○ | ○ | ○ | ○ | ○ | ○ | ○ | ○ | ○ | ○ | ○ |
| Example 3 | ○ | ○ | ○ | ○ | ○ | ○ | ○ | ○ | ○ | ○ | ○ | ○ |
| Example 4 | ○ | ○ | ○ | ○ | ○ | ○ | ○ | ○ | ○ | ○ | ○ | ○ |
| Example 5 | ○ | ○ | ○ | ○ | ○ | ○ | ○ | ○ | ○ | ○ | ○ | ○ |
| Example 6 | ○ | ○ | ○ | ○ | ○ | ○ | ○ | ○ | ○ | ○ | ○ | ○ |
| Comparative Example 1 | ○ | ○ | ○ | ○ | ○ | ○ | Δ | ○ | ○ | ○ | Δ | ○ |
| Comparative Example 2 | ○ | ○ | ○ | ○ | ○ | ○ | Δ | ○ | ○ | ○ | Δ | ○ |
| Comparative Example 3 | ○ | Δ | ○ | Δ | Δ | ○ | X | Δ | Δ | ○ | X | Δ |
| Comparative Example 4 | ○ | Δ | ○ | Δ | Δ | ○ | X | Δ | Δ | ○ | X | Δ |
| Comparative Example 5 | ○ | Δ | ○ | Δ | ○ | ○ | Δ | ○ | Δ | ○ | Δ | ○ |
| Comparative Example 6 | Δ | Δ | Δ | Δ | X | X | X | Δ | X | Δ | X | Δ |

TABLE 2

| | Initial emulsifiabiity | | | | Emulsified stability | | | | | | | |
|---|---|---|---|---|---|---|---|---|---|---|---|---|
| | | | | | Hard water of 3° | | | | Hard water of 19.2° | | | |
| | Hard water of 3° | | Hard water of 19.2° | | After 2 hours | | After 24 hours | | After 2 hours | | After 24 hours | |
| Example No. | ×20 | ×200 | ×20 | ×200 | ×20 | ×200 | ×20 | ×200 | ×20 | ×200 | ×20 | ×200 |
| Example 1 | ○ | ○ | ○ | ○ | ○ | ○ | ○ | ○ | ○ | ○ | ○ | ○ |
| Example 2 | ○ | ○ | ○ | ○ | ○ | ○ | ○ | ○ | ○ | ○ | ○ | ○ |
| Example 3 | ○ | ○ | ○ | ○ | ○ | ○ | ○ | ○ | ○ | ○ | ○ | ○ |
| Example 4 | ○ | ○ | ○ | ○ | ○ | ○ | ○ | ○ | ○ | ○ | ○ | ○ |
| Example 5 | ○ | ○ | ○ | ○ | ○ | ○ | ○ | ○ | ○ | ○ | ○ | ○ |
| Example 6 | ○ | ○ | ○ | ○ | ○ | ○ | ○ | ○ | ○ | ○ | ○ | ○ |
| Comparative Example 1 | ○ | ○ | ○ | ○ | Δ | ○ | X | Δ | Δ | ○ | X | Δ |
| Comparative Example 2 | ○ | ○ | ○ | ○ | Δ | ○ | X | Δ | Δ | ○ | X | Δ |
| Comparative Example 3 | ○ | Δ | ○ | Δ | X | Δ | X | Δ | X | Δ | X | Δ |
| Comparative Example 4 | ○ | Δ | ○ | Δ | X | Δ | X | Δ | X | Δ | X | Δ |
| Comparative Example 5 | ○ | Δ | ○ | Δ | X | Δ | X | Δ | X | Δ | X | Δ |
| Comparative Example 6 | X | Δ | X | Δ | X | Δ | X | Δ | X | Δ | X | Δ |

As shown in Tables 1 and 2, the products of the present invention are superior in the initial emulsifiability or in the emulsified stability to a conventional emulsifiable concentrate using an organic solvent (Comparative Example 1), a flowable formulation (Comparative Example 2) and conventional emulsifiable concentrates using no organic solvents (Comparative Examples 3 to 6).

TEST EXAMPLE 2: Test for stability with time of the active ingredient

Samples formulated in accordance with various formulation methods, were put in glass ampules and stored at 40° C. for 90 days, whereby the changes in the content of the active ingredients were obtained by gas chromatography. The results are shown in Table 3.

TABLE 3

| Example No. | Active ingredient | Initial analytical value | Analytical values after 90 days at 40° C. | Decomposition rate |
|---|---|---|---|---|
| Example 1 | Compound (1) | 90.2 | 90.0 | 0.2 |
| Example 2 | Compound (1) | 94.1 | 93.8 | 0.3 |
| Example 3 | Compound (2) | 92.4 | 92.4 | 0.0 |
| Example 4 | Compound (3) | 91.9 | 91.5 | 0.4 |
| Example 5 | Compound (4) | 92.1 | 91.0 | 1.2 |
| Example 6 | Compound (1) | 72.8 | 72.2 | 0.8 |
| | Symmetrine | 12.6 | 12.3 | 2.4 |
| | MCPB-E | 6.65 | 6.61 | 0.6 |
| Comparative Example 1 | Compound (1) | 53.4 | 52.7 | 1.3 |
| Comparative Example 2 | Compound (1) | 53.1 | 50.7 | 4.5 |
| Comparative Example 3 | Compound (1) | 90.3 | 90.1 | 0.2 |
| Comparative Example 4 | Compound (1) | 90.7 | 90.2 | 0.6 |
| Comparative Example 5 | Compound (1) | 90.4 | 89.4 | 1.1 |
| Comparative Example 6 | Compound (1) | 90.8 | 90.3 | 0.6 |

As shown in Table 3, the stabilities with time of the active ingredients of the products of the present invention are excellent in that they are stable as compared with a conventional emulsifiable concentrate using an organic solvent (Comparative Example 1), a flowable formulation (Comparative Example 2) and conventional emulsifiable concentrates using no organic solvents (Comparative Examples 3 to 6).

TEST EXAMPLE 3: Test for biological effects (1) Dry field direct seeding treatment Into a 1/1,500a container, rice and edible barnyard grass were seeded separately. On the 16th day after the seeding, each formulation of Compound (1) as identified in Table 4 was diluted with water to a predetermined concentration and applied to the foliages at a rate of 100 l/hr by means of a hand sprayer. On the 30th day, the foliages above ground level of the rice and the edible barnyard grass were harvested, and the dry weights were measured. The results are shown in Table 4.

Test plants: Rice (Kinmaze, 1.5-1.8 leaf stage, 15 plants/container) Barnyard grass (edible barnyard grass, 1.8-2.0 leaf stage, 15 plants/container)

(2) Paddy field direct seeding treatment

In a 1/500a container, rice and edible barnyard grass were seeded separately. On the 14th day after the seeding, water was introduced to a water depth of 3 cm, and then each formulation of compound (1) as identified in Table 4 was diluted with water to a predetermined concentration and applied by dropwise addition by means of pipet. On the 30th day after the application, the foliages of the rice and the edible barnyard grass above ground level were harvested, and the dry weights were measured. The results are shown in Table 4.

Test plants: Rice (Kinmaze, 1.5-1.8 leaf stage, 15 plants/container) Barnyard grass (edible barnyard grass, 1.8-2.0 leaf stage, 15 plants/container)

Since no organic solvent is employed, the products of the present invention are free from phytotoxicity to crop plants due to the contact of an organic solvent, whereby the selectivity is improved.

TEST EXAMPLE 4: Test for freezing resistance and heat resistance

Samples formulated in each Example were put in glass bottles having a capacity of 100 ml and stored for 30 days at $-5°$ C., at $-25°$ C. and at 50° C. Then, they were left to stand at room temperature (25° C.) for 6 hours. Thereafter, the changes in the color and outer appearance and the initial emulsifiabilities were examined. The results are shown in Table 5.

Evaluation method

TABLE 4

| Example No. | Compound (1) Dose of active ingredient (kg/ha) | Dry field direct seeding treatment | | Paddy field direct seeding treatment | |
|---|---|---|---|---|---|
| | | Ratio of the dry weight of the foliage of rice to non-treated area (%) | Ratio of the dry weight of the foliage of barnyard grass to non-treated area (%) | Ratio of the dry weight of the foliage of rice to non-treated area (%) | Ratio of the dry weight of the foliage of barnyard grass to non-treated area (%) |
| Example 1 | 3 | 102.4 | 5.7 | 94.6 | 3.2 |
| Example 2 | 3 | 104.1 | 5.3 | 97.2 | 3.1 |
| Example 6 | 3 | 97.8 | 1.3 | 90.1 | 0.5 |
| Comparative Example 1 | 3 | 93.4 | 6.5 | 93.7 | 4.1 |
| Comparative Example 2 | 3 | 98.9 | 10.5 | 94.1 | 7.6 |
| Comparative Example 3 | 3 | 101.2 | 7.9 | 95.4 | 4.3 |
| Comparative Example 4 | 3 | 100.9 | 6.2 | 94.6 | 3.9 |
| Comparative Example 5 | 3 | 99.8 | 8.6 | 94.0 | 4.2 |
| Comparative Example 6 | 3 | 102.2 | 7.7 | 92.2 | 5.2 |
| Non-treatment area | — | 100.0 | 100.0 | 100.0 | 100.0 |

As shown in Table 4, the biological effects of the products of the present invention are excellent as compared with a conventional emulsifiable concentrate employing an organic solvent (Comparative Example 1), a flowable formulation (Comparative Example 2) and conventional emulsifiable concentrates employing no organic solvent (Comparative Examples 3 to 6).

Changes in the color and outer appearance
◯ : No change Initial emulsifiability (Hard water of 3°, diluted 100 times)
◯ : Excellent self emulsifiability
△: Slightly poor self emulsifiability
X: Poor self emulsifiability

TABLE 5

| Example No. | Changes in color and outer appearance | | | Initial emulsifiability | | |
|---|---|---|---|---|---|---|
| | $-5°$ C. | $-25°$ C. | 50° C. | $-5°$ C. | $-25°$ C. | 50° C. |
| Example 1 | ◯ | ◯ | ◯ | ◯ | ◯ | ◯ |
| Example 2 | ◯ | ◯ | ◯ | ◯ | ◯ | ◯ |
| Example 3 | ◯ | ◯ | ◯ | ◯ | ◯ | ◯ |
| Example 4 | ◯ | ◯ | ◯ | ◯ | ◯ | ◯ |
| Example 5 | ◯ | ◯ | ◯ | ◯ | ◯ | ◯ |
| Example 6 | ◯ | ◯ | ◯ | ◯ | ◯ | ◯ |
| Comparative Example 1 | ◯ | ◯ | ◯ | ◯ | ◯ | ◯ |
| Comparative Example 2 | ◯ | Separation | Precipitation | ◯ | ◯ | △ |
| Comparative Example 3 | ◯ | ◯ | ◯ | ◯ | ◯ | △ |
| Comparative Example 4 | ◯ | ◯ | ◯ | ◯ | ◯ | △ |
| Comparative Example 5 | ◯ | ◯ | ◯ | ◯ | ◯ | △ |
| Comparative Example 6 | ◯ | ◯ | ◯ | ◯ | ◯ | △ |

As shown in Table 5, the freezing resistance and heat resistance of the products of the present invention are excellent as compared with a conventional emulsifier employing an organic solvent (Comparative Example 1), a flowable formulation (Comparative Example 2) and conventional emulsifiable concentrates employing no organic solvent (Comparative Examples 3 to 6).

We claim:

1. A high concentration herbicide formulation comprising (1) a herbicidally active thiolcarbamate of the following formula I which is liquid at room temperature, (2) at least one nonionic surfactant of the following formula II and (3) an anionic surfactant of the following formula III:

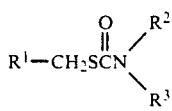
(I)

wherein $R^1$ is an alkyl group having from 1 to 8 carbon atoms, a phenyl group or a halogen-substituted phenyl group, $R^2$ is an alkyl group having from 1 to 5 carbon atoms, and $R^3$ is an alkyl group having from 1 to 5 carbon atoms, provided that $R^2$ and $R^3$ may form a ring;

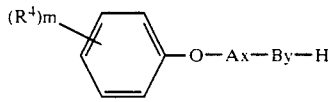
(II)

wherein $R^4$ is

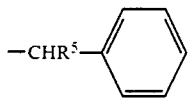

wherein $R^5$ is a hydrogen atom or a methyl group, m is an integer of from 1 to 3, x is an integer of at least 10, y is an integer of from 0 to 10, provided that $x+y$ is within a range of from 10 to 30, A is an oxyethylene group, and B is an oxypropylene group, provided that the addition form of A and B may be a block-form or a random-form; and

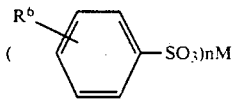
(III)

wherein $R^6$ is an alkyl group having from 9 to 15 carbon atoms, M is an alkali metal or an alkaline earth metal, and n is the number of metal ions.

2. The high concentration herbicide formulation according to claim 1, wherein the herbicidally active thiolcarbamate is S-(4-chlorobenzyl)-N,N-diethylthiolcarbamate or S-(2-chlorobenzyl)-N,N-diethylthiolcarbamate.

3. The high concentration herbicide formulation according to claim 1, wherein the nonionic surfactant is a polyoxyalkylene styrylphenyl ether having a HLB value within a range of from 12 to 15.

4. The high concentration herbicide formulation according to claim 1, wherein the anionic surfactant is a calcium salt of dodecylbenzene sulfonate.

* * * * *